United States Patent [19]

Oroskar

[11] Patent Number: 5,476,980
[45] Date of Patent: Dec. 19, 1995

[54] PROCESS FOR THE DEHYDROGENATION OF A DEHYDROGENATABLE HYDROCARBON

[75] Inventor: Anil R. Oroskar, Downers Grove, Ill.

[73] Assignee: UOP, Des Plaines, Ill.

[21] Appl. No.: 363,071

[22] Filed: Dec. 23, 1994

[51] Int. Cl.[6] .................................................. C07C 5/42
[52] U.S. Cl. ..................... 585/654; 585/617; 585/634; 585/656
[58] Field of Search ............................... 585/654, 634, 585/656, 617

[56] References Cited

U.S. PATENT DOCUMENTS 4,511,754  4/1985  Gaffney .................................. 585/656
4,560,823  12/1985  Gaffney .................................. 585/654
4,675,465  6/1987  Fanelli et al. .......................... 585/654

*Primary Examiner*—Asok Pal
*Assistant Examiner*—Bekir L. Yildirim
*Attorney, Agent, or Firm*—Thomas K. McBride; John G. Tolomei; John G. Cutts, Jr.

[57] ABSTRACT

A process for the dehydrogenation of a dehydrogenatable hydrocarbon by contacting the hydrocarbon with a liquid comprising an alkali metal in a dehydrogenation zone to produce a dehydrogenated hydrocarbon and an alkali metal halide. The resulting alkali metal hydride is heated to produce a heated liquid alkali metal and hydrogen. The heated liquid alkali metal is recycled to the dehydrogenation zone to provide heat and elemental metal.

7 Claims, 1 Drawing Sheet

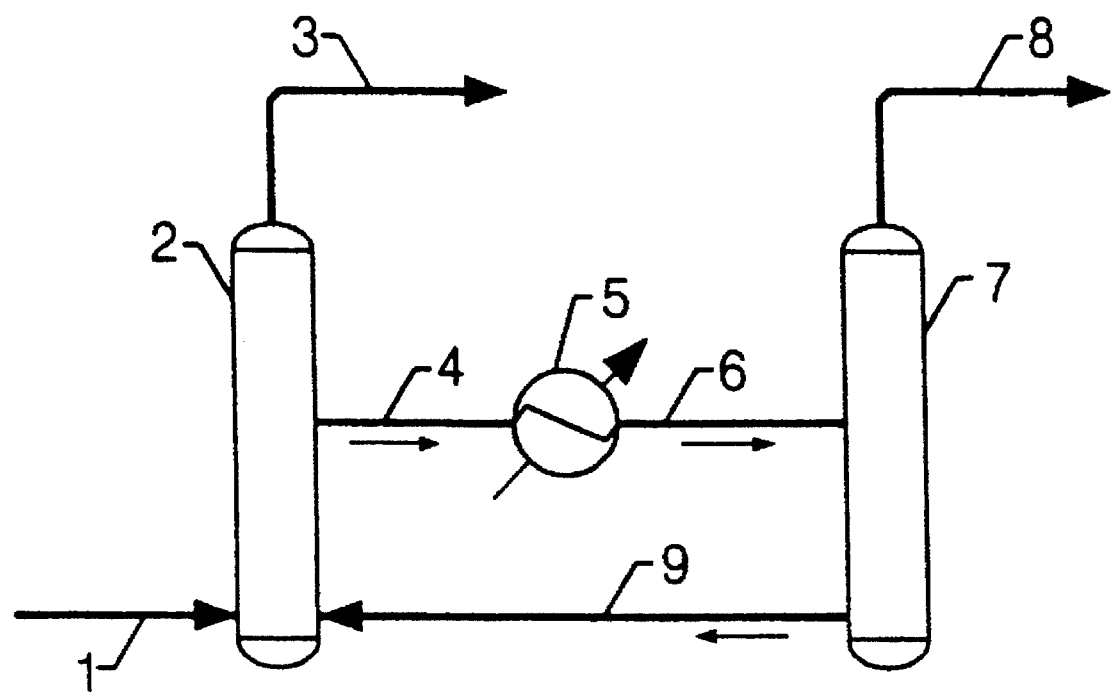

PROCESS FOR THE DEHYDROGENATION OF A DEHYDROGENATABLE HYDROCARBON

FIELD OF THE INVENTION

The field of art to which this invention pertains is the production of olefinic hydrocarbons by the dehydrogenation of dehydrogenatable hydrocarbons. This invention relates more specifically to a process for the dehydrogenation of a dehydrogenatable hydrocarbon by contacting the dehydrogenatable hydrocarbon with a liquid comprising an alkali metal in a dehydrogenation zone to produce a dehydrogenated hydrocarbon and an alkali metal hydride. The resulting alkali metal hydride is heated to produce a heated liquid alkali metal and hydrogen. The heated liquid alkali metal is recycled to the dehydrogenation zone to provide heat.

There is a steadily increasing demand for technology which is capable of producing olefins from dehydrogenatable hydrocarbons containing from 2 to about 18 carbon atoms. Dehydrogenating hydrocarbons is an important commercial hydrocarbon conversion process because of the great demand for dehydrogenated hydrocarbons for the manufacture of various chemical products such as detergents, high octane motor fuels, pharmaceutical products, plastics, synthetic rubbers, polymerization and other products well known to those skilled in the art. Processes for the dehydrogenation of light acyclic hydrocarbons are well known to those skilled in the hydrocarbon conversion arts.

INFORMATION DISCLOSURE

In U.S. Pat. No. 4,675,465 (Fanelli et al.), a process is disclosed for dehydrogenating reactants wherein a reactant comprising a hydrocarbon is exposed to a solid admixture of a platinum on alumina catalyst for dehydrogenation and a material to remove at least one hydrogen atom from the hydrocarbon and form a material hydride. The material is selected from the group of metals, alloys and intermetallic compounds having a negative free energy of formation for a hydrided product. The '465 patent fails to disclose the contacting of a dehydrogenatable hydrocarbon with a liquid comprising an alkali metal in a dehydrogenation zone to produce a dehydrogenated hydrocarbon and an alkali metal halide.

Other prior art processes for the dehydrogenation of paraffins suffered under several disadvantages including poor olefin product yields and poor catalyst life caused by the relatively high catalyst inlet temperature required to supply the essential heat of reaction and the relatively high cost of the required multi-stage reactors and their attendant interheaters.

BRIEF SUMMARY OF THE INVENTION

The invention provides a process for the dehydrogenation of a dehydrogenatable hydrocarbon by contacting the dehydrogenatable hydrocarbon with a liquid comprising an alkali metal in a dehydrogenation zone to produce a dehydrogenated hydrocarbon an alkali metal halide. At least a portion of the resulting alkali metal hydride is heated to produce a heated liquid alkali metal and hydrogen. At least a portion of the heated liquid alkali metal is recycled to the dehydrogenation zone to provide heat. The present invention provides a convenient and economical process for the production of olefinic hydrocarbons. Important elements of the process are the facile removal of hydrogen from the dehydrogenation zone which minimizes chemical equilibrium constraints and simplifies the recovery of the resulting olefinic hydrocarbons and the supply of heat to the dehydrogenation zone without the need to heat the dehydrogenatable hydrocarbon reactants to reaction temperature prior to entering the reaction zone.

One embodiment of the present invention may be characterized as a process for the dehydrogenation of a dehydrogenatable hydrocarbon which process comprises: (a) contacting the dehydrogenatable hydrocarbon with a liquid comprising an alkali metal in a dehydrogenation zone at dehydrogenation conditions to produce a dehydrogenated hydrocarbon and an alkali metal hydride; (b) removing and heating at least a portion of the alkali metal hydride from the dehydrogenation zone to produce a heated liquid alkali metal and hydrogen; (c) recycling at least a portion of the heated liquid alkali metal to the dehydrogenation zone in step (a); and (d) recovering the dehydrogenated hydrocarbon.

BRIEF DESCRIPTION OF THE DRAWING

The drawing is a simplified process flow diagram of a preferred embodiment of the present invention.

DETAILED DESCRIPTION OF THE INVENTION

The present invention provides a process for the dehydrogenation of a dehydrogenatable hydrocarbon. The dehydrogenatable hydrocarbon is contacted with a liquid comprising an alkali metal in a dehydrogenation zone at dehydrogenation conditions to produce a dehydrogenated hydrocarbon and an alkali metal hydride. The dehydrogenated hydrocarbon is preferably removed from the dehydrogenation zone in gaseous phase and the alkali metal hydride is removed from the dehydrogenation zone in a liquid phase. The alkali metal hydride is subsequently heated to remove hydrogen thereby providing heated metal which may be recycled to serve as a hydrogen sponge and to provide heat for the endothermic dehydrogenation reaction in the dehydrogenation zone.

Paraffin dehydrogenation is an endothermic reaction and the heat of reaction for the formation of a mono-olefin is approximately 30 kilocalories/gram mol for a feed that may vary from $C_2$ (ethane) to $C_{18}$ paraffins. Therefore, when olefins are produced from paraffins, the heat of reaction must be supplied from an external source.

In accordance with the present invention, the dehydrogenatable hydrocarbon charge stock may contain from 2 carbon atoms to about 18 carbon atoms. Representative members of this class are ethane, propane, butane, pentane, hexane, heptane and mixtures thereof. A particularly important class of charge stocks include propane, butane, pentane and mixtures thereof and which are readily prepared by the fractionation of relatively low boiling point hydrocarbon fractions.

The dehydrogenatable hydrocarbon feedstock is introduced into a dehydrogenation zone and contacted with a liquid comprising an alkali metal at dehydrogenation conditions to produce a dehydrogenated hydrocarbon and an alkali metal halide. Preferred dehydrogenation conditions include a pressure from atmospheric to about 500 psig (3447 kPa gauge), a temperature from about 392° F. (200° C.) to about 1310° F. (700° C.), and a metal to hydrocarbon mole ratio from about 1 to about 20.

A resulting hydrocarbon stream containing olefin hydrocarbons is removed from the dehydrogenation zone and recovered. In a preferred embodiment, the resulting hydrocarbon stream is separated to recover the olefin hydrocarbons and to produce a stream of unreacted hydrocarbons which may then be recycled to the dehydrogenation zone to produce additional olefin hydrocarbons.

A liquid stream containing alkali metal halide is removed from the dehydrogenation zone and is heated to produce a heated liquid alkali metal stream and hydrogen. In order to regenerate the alkali metal halide stream, it is preferably heated in a heating zone to a temperature in the range from about 752° F. (400° C.) to about 1562° F. (850° C.). The circulation rate of the heated liquid alkali metal stream is preferably selected to ensure that the required heat is subsequently supplied to the dehydrogenation zone to maintain the desired dehydrogenation reaction temperature.

In accordance with the present invention, the alkali metal may be selected from the group consisting of lithium, sodium, potassium, rubidium, cesium and admixtures thereof. In one embodiment of the present invention, the circulating liquid stream containing alkali metal and/or alkali metal halide may be transferred to and from the dehydrogenation zone and the heating zone by means of pumps, gravity or thermal siphon.

In the drawing, the process of the present invention is illustrated by means of a simplified flow diagram in which such details as total number of reaction zones, heating zones, pumps, instrumentation, heat-exchange and heat-recovery circuits, compressors and similar hardware have been deleted as being non-essential to an understanding of the techniques involved. The use of such miscellaneous equipment is well within the purview of one skilled in the art.

DETAILED DESCRIPTION OF THE DRAWING

With reference now to the drawing, a dehydrogenatable hydrocarbon is introduced into the dehydrogenation zone 2 via conduit 1 and contacted with a heated liquid stream containing alkali metal which is introduced via conduit 9 into dehydrogenation zone 2. A resulting gaseous hydrocarbon stream containing olefin hydrocarbons is removed from dehydrogenation zone 2 via conduit 3 and recovered. A liquid stream containing alkali metal hydride is removed from dehydrogenation zone 2 via conduit 4 and introduced into heat exchanger 5. A heated effluent from heat exchanger 5 is transported via conduit 6 and introduced into vapor-liquid separator 7. A gaseous stream containing molecular hydrogen is removed from vapor-liquid separator 7 via conduit 8. A liquid stream containing alkali metal is removed from vapor-liquid separator 7 via conduit 9 and introduced into dehydrogenation zone 2 as described hereinabove.

EXAMPLE

A pilot plant autoclave was charged with lithium and heated to 932° F. (500° C.). A pure isobutane feedstock was introduced below the surface of the liquid lithium and the pressure in the autoclave was maintained at 50 psig. A gaseous product was continuously withdrawn from the autoclave and analyzed. The characteristics of the gaseous product are presented in Table 1.

TABLE 1

| PRODUCT ANALYSIS | |
|---|---|
| Isobutane, weight percent | 94.5 |
| Propane, weight percent | 0.5 |
| Isobutylene, weight percent | 4.5 |
| Hydrogen, weight percent | 0 |

From Table 1, it can readily be seen that when isobutane is contacted with liquid lithium at a temperature of 932° F. and a pressure of 50 psig, 4.5 weight percent isobutylene is produced. Moreover, no hydrogen is seen in the gaseous product, as it remains in the liquid as lithium hydride. Therefore, the conclusion is drawn that two atoms of lithium react with a molecule of isobutane to produce two molecules of lithium hydride and one molecule of isobutylene.

The foregoing description, drawing and example clearly illustrate the advantages encompassed by the method of the present invention and the benefits to be afforded with the use thereof.

What is claimed:

1. A process for the dehydrogenation of a dehydrogenatable hydrocarbon which process comprises:

(a) contacting said dehydrogenatable hydrocarbon with a liquid comprising an alkali metal in a dehydrogenation zone at dehydrogenation conditions to produce a dehydrogenated hydrocarbon and an alkali metal hydride;

(b) removing and heating at least a portion of said alkali metal hydride from said dehydrogenation zone to produce a heated liquid alkali metal and hydrogen;

(c) recycling at least a portion of said heated liquid alkali metal to said dehydrogenation zone in step (a); and (d) recovering said dehydrogenated hydrocarbon.

2. The process of claim 1 wherein said alkali metal is selected from the group consisting of lithium, sodium, potassium, rubidium and cesium.

3. The process of claim 1 wherein said dehydrogenation conditions include a pressure from about atmospheric to about 500 psig (3447 kPa gauge), a temperature from about 392° F. (200° C.) to about 1310° F. (700° C.), a hydrocarbon to alkali metal mol ratio from about 1 to about 20.

4. The process of claim 1 wherein said alkali metal hydride is heated to a temperature in the range from about 752° F. (400° C.) to about 1562° F. (850° C.) to produce said heated liquid alkali metal and said hydrogen.

5. The process of claim 1 wherein said dehydrogenatable hydrocarbon is an alkane having from 2 to about 18 carbon atoms.

6. The process of claim 1 wherein said dehydrogenated hydrocarbon is an alkene.

7. The process of claim 1 wherein said dehydrogenated hydrocarbon is an alkyne.

\* \* \* \* \*